(12) United States Patent
Davis et al.

(10) Patent No.: US 11,166,677 B2
(45) Date of Patent: Nov. 9, 2021

(54) SYSTEMS AND METHODS FOR MONITORING A PATIENT

(71) Applicant: General Electric Company, Schenectady, NY (US)

(72) Inventors: Cynthia Elizabeth Landberg Davis, Niskayuna, NY (US); Esmaeil Heidari, Lake Forest, CA (US); Aghogho Obi, Troy, NY (US); John Eric Tkaczyk, Delanson, NY (US)

(73) Assignee: GENERAL ELECTRIC COMPANY, Schenectady, NY (US)

( * ) Notice: Subject to any disclaimer, the term of this patent is extended or adjusted under 35 U.S.C. 154(b) by 316 days.

(21) Appl. No.: 16/294,694

(22) Filed: Mar. 6, 2019

(65) Prior Publication Data

US 2020/0281532 A1 Sep. 10, 2020

(51) Int. Cl.
*A61B 5/00* (2006.01)
*A61B 5/0205* (2006.01)
(Continued)

(52) U.S. Cl.
CPC ............ *A61B 5/6891* (2013.01); *A61B 5/024* (2013.01); *A61B 5/02055* (2013.01);
(Continued)

(58) Field of Classification Search
CPC ... A61B 5/6891; A61B 5/02055; A61B 5/024; A61B 5/0816; A61B 5/318; A61B 5/01;
(Continued)

(56) References Cited

U.S. PATENT DOCUMENTS 3,920,000 A 11/1975 Atherton et al.
5,446,934 A 9/1995 Frazier
(Continued)

FOREIGN PATENT DOCUMENTS

GB 2494992 B 10/2016

OTHER PUBLICATIONS

PCT application PCT/US2020/020931 filed Mar. 4, 2020—International Search Report/Written Opinion dated Jun. 19, 2020; 11 pages.
(Continued)

*Primary Examiner* — Navin Natnithithadha
*Assistant Examiner* — Sunita Reddy
(74) *Attorney, Agent, or Firm* — Fletcher Yoder, P.C.

(57) ABSTRACT

The disclosed systems and methods for monitoring a patient in a medical setting may include various types of sensors that obtain data indicative of one or more patient parameters and one or more environmental parameters. One or more processors may process the data to identify a correlation, or causal relationship, between the one or more patient parameters and the one or more environmental parameters. Thus, the systems and methods may be used to identify particular environmental parameters that affect a particular patient to facilitate creation of a suitable environment for the particular patient. The disclosed monitoring systems and methods may be especially useful for sensitive, high-risk, and/or non-verbal patients, such as infants in a neonatal intensive care unit (NICU).

15 Claims, 4 Drawing Sheets

(51) Int. Cl.
  *A61B 5/024* (2006.01)
  *A61B 5/08* (2006.01)
  *A61G 11/00* (2006.01)
  *G16H 50/30* (2018.01)
  *A61B 5/01* (2006.01)
  *A61B 5/11* (2006.01)
  *A61B 5/318* (2021.01)

(52) U.S. Cl.
  CPC ............ *A61B 5/0816* (2013.01); *A61G 11/00* (2013.01); *G16H 50/30* (2018.01); *A61B 5/01* (2013.01); *A61B 5/11* (2013.01); *A61B 5/318* (2021.01); *A61B 2503/045* (2013.01)

(58) Field of Classification Search
  CPC .............. A61B 5/11; A61B 2503/0233; A61B 2560/0252; A61B 2562/0219; A61B 2562/0261; A61B 5/742; A61B 5/14542; A61B 5/002; A61B 5/1116; A61B 5/1115; A61B 2562/0204; G16H 50/30; A61G 11/00
  USPC ...................................................... 600/21–22
  See application file for complete search history.

(56) References Cited

U.S. PATENT DOCUMENTS

| | | | |
|---|---|---|---|
| 5,730,355 A | 3/1998 | Lessard et al. | |
| 5,971,913 A * | 10/1999 | Newkirk | G05D 23/1917 600/22 |
| 8,361,000 B2 | 1/2013 | Gaspard | |
| 9,247,346 B2 | 1/2016 | Kuo et al. | |
| 9,452,235 B2 | 9/2016 | Veen et al. | |
| 2002/0173696 A1* | 11/2002 | Kolarovic | A61B 5/01 600/22 |
| 2002/0196141 A1* | 12/2002 | Boone | A61G 7/0503 340/540 |
| 2004/0236174 A1* | 11/2004 | Boone | A61G 11/00 600/21 |
| 2005/0215844 A1* | 9/2005 | Ten Eyck | A61B 5/02055 600/22 |
| 2007/0086506 A1* | 4/2007 | Dicks | G01J 5/089 374/121 |
| 2009/0149927 A1* | 6/2009 | Kneuer | G05D 23/00 607/96 |
| 2012/0157796 A1* | 6/2012 | Ten Eyck | A61G 11/005 600/22 |
| 2013/0150655 A1* | 6/2013 | Ten Eyck | A61G 11/003 600/22 |
| 2013/0158339 A1* | 6/2013 | Cipriano | A61G 11/009 600/22 |
| 2014/0179984 A1* | 6/2014 | Cipriano | A61G 11/00 600/22 |
| 2014/0371635 A1* | 12/2014 | Shinar | A61B 5/6892 600/595 |
| 2015/0182406 A1* | 7/2015 | Falk | G06F 19/00 600/22 |
| 2017/0000347 A1* | 1/2017 | Meftah | A61B 5/6892 |

OTHER PUBLICATIONS

Almadhoob, Abdulraoof, et al.; "Sound reduction management in the neonatal intensive care unit for preterm or very low birth weight infants", Cochrane database of systematic reviews , pp. 1-25, Jan. 2015.

Shakunthala, M., et al.; "Neonatal healthcare monitoring in incubator using Iot", International Journal of Electrical, Electronics and Data Communication, pp. 1-6, vol. 06, Issue: 6, Jun. 2018.

Steinhubl, Steven R., et al.; "Remote sensing of vital signs: a wearable, wireless "band-aid" sensor with personalized analytics for improved Ebola patient care and worker safety", Glob Health Sci Pract. 2015; 3(3): pp. 516-519.

1080p HD Baby Monitoring Camera: Arlo Baby. Netgear, Inc. Accessed Mar. 6, 2019 at www.arlo.com. 6 pages.

Nanit Plus Camera. Nanit. 2017. Accessed at www.nanit.com. 19 pages.

* cited by examiner

SYSTEMS AND METHODS FOR MONITORING A PATIENT

BACKGROUND

The subject matter disclosed herein relates to systems and methods for monitoring a patient in a medical setting.

This section is intended to introduce the reader to various aspects of art that may be related to various aspects of the present techniques, which are described and/or claimed below. This discussion is believed to be helpful in providing the reader with background information to facilitate a better understanding of the various aspects of the present disclosure. Accordingly, it should be understood that these statements are to be read in this light, and not as admissions of prior art.

A patient in a medical setting, such as an infant in a neonatal intensive care unit (NICU), may be monitored using various types of sensors. For example, the patient may be monitored via one or more sensors that measure one or more physiological parameters (e.g., a heart rate, respiratory rate, and/or oxygen saturation).

BRIEF DESCRIPTION

Certain embodiments commensurate in scope with the originally claimed disclosure are summarized below. These embodiments are not intended to limit the scope of the claimed disclosure, but rather these embodiments are intended only to provide a brief summary of possible forms of the disclosure. Indeed, embodiments may encompass a variety of forms that may be similar to or different from the embodiments set forth below.

In one embodiment, a system includes a memory or storage structure storing one or more processor-executable routines and one or more processors configured to execute the one or more processor-executable routines stored in the memory or storage structure. The one or more processor-executable routines, when executed, cause the one or more processors to perform acts that include receiving a first signal indicative of an environmental parameter of an environment, receiving a second signal indicative of a patient parameter of a patient, analyzing the first signal and the second signal to determine a causal relationship between the environmental parameter and the patient parameter, and providing an output indicative of the causal relationship via a display screen.

In one embodiment, an incubator system configured to house an infant includes a frame, a cover configured to be coupled to the frame to cover a bed, and multiple sensors supported on the frame, positioned within the cover, or both. The multiple sensors are configured to monitor one or more environmental parameters of an environment around the infant and to monitor one or more patient parameters of the infant. The multiple sensors include one or more accelerometers configured to detect a motion of the bed of the infant, one or more microphones configured to detect an ambient sound and a sound of the infant, and one or more infrared thermometers or cameras configured to detect an ambient temperature and a body temperature of the infant.

In one embodiment, a method includes receiving, at one or more processors, a first signal indicative of an environmental parameter of an environment. The method includes receiving, at the one or more processors, a second signal indicative of a patient parameter of a patient. The method also includes analyzing, using the one or more processors, the first signal and the second signal to determine a causal relationship between the environmental parameter and the patient parameter. The method further includes providing, using the one or more processors, an output indicative of the causal relationship via a display screen.

BRIEF DESCRIPTION OF THE DRAWINGS

These and other features, aspects, and advantages of the present disclosure will become better understood when the following detailed description is read with reference to the accompanying drawings in which like characters represent like parts throughout the drawings, wherein.

DETAILED DESCRIPTION

Figure 1:
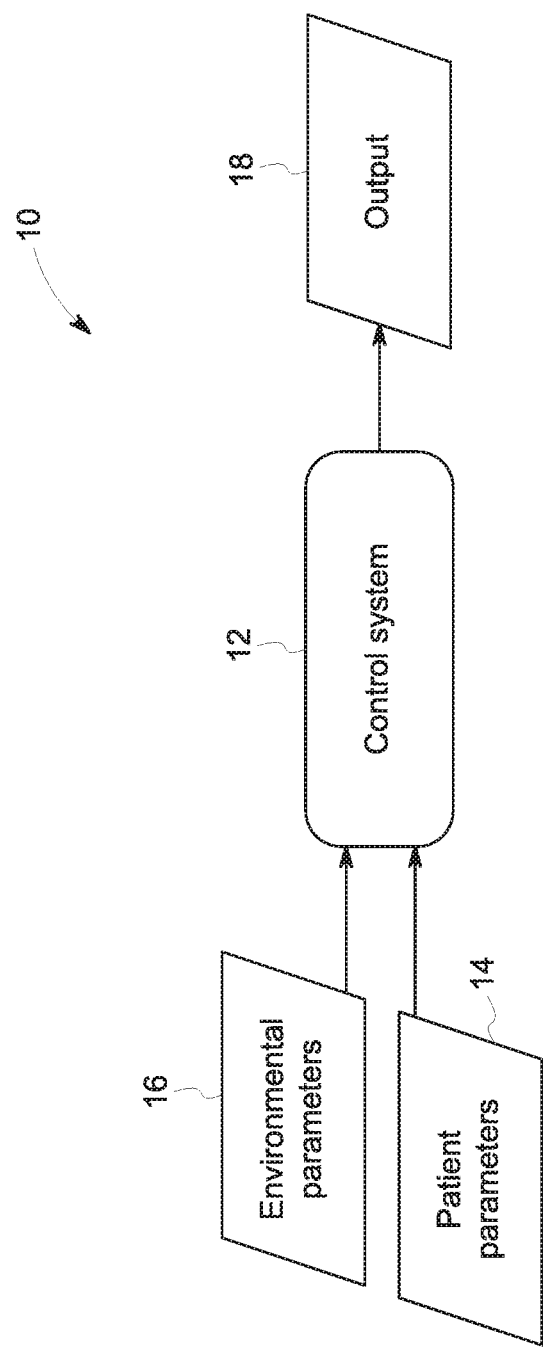
FIG. 1 is a block diagram of a patient monitoring system, in accordance with an embodiment of the present disclosure.

One or more specific embodiments of the present disclosure will be described below. In an effort to provide a concise description of these embodiments, all features of an actual implementation may not be described in the specification. It should be appreciated that in the development of any such actual implementation, as in any engineering or design project, numerous implementation-specific decisions must be made to achieve the developers' specific goals, such as compliance with system-related and business-related constraints, which may vary from one implementation to another. Moreover, it should be appreciated that such a development effort might be complex and time consuming, but would nevertheless be a routine undertaking of design, fabrication, and manufacture for those of ordinary skill having the benefit of this disclosure.

When introducing elements of various embodiments of the present disclosure, the articles "a," "an," "the," and "said" are intended to mean that there are one or more of the elements. The terms "comprising," "including," and "having" are intended to be inclusive and mean that there may be additional elements other than the listed elements. One or more specific embodiments of the present embodiments described herein will be described below. In an effort to provide a concise description of these embodiments, all features of an actual implementation may not be described in the specification. It should be appreciated that in the development of any such actual implementation, as in any engineering or design project, numerous implementation-specific decisions must be made to achieve the developers' specific goals, such as compliance with system-related and business-related constraints, which may vary from one implementation to another. Moreover, it should be appreciated that such a development effort might be complex and time consuming, but would nevertheless be a routine undertaking of design, fabrication, and manufacture for those of ordinary skill having the benefit of this disclosure.

Embodiments of the present disclosure relate to systems and methods for monitoring a patient in a medical setting. More particularly, certain embodiments of the present disclosure relate to a monitoring system that includes various types of sensors that obtain data indicative of one or more patient parameters (e.g., heart rate, other heart parameters, respiratory rate, oxygen saturation rate, brain activity, body temperature, sounds from the patient, and/or motion of the patient) and one or more environmental parameters (e.g., ambient temperature, ambient light, ambient sounds, and/or motion of the bed of the patient). Advantageously, at least some of the sensors may not contact the patient, which may reduce interference with other equipment and/or may reduce irritation to the skin of the patient.

The monitoring system may include one or more processors that process the data to identify a correlation (e.g., causal relationship) between the one or more patient parameters and the one or more environmental parameters. For example, the data may indicate that an increase in the heart rate of the patient followed a loud ambient sound, and thus, the one or more processors may determine that the increase in the heart rate of the patient was likely caused by, or otherwise observationally correlated with, the loud ambient sound. The one or more processors may also instruct an output device (e.g., display screen and/or speaker) to output an indication of the correlation. For example, the output may include a text message on a display screen that indicates that the increase in the heart rate of the patient was likely caused by the loud ambient sound. The output may include or illustrate signal features (e.g., co-occurring or near in time) and/or signal trends over time for the correlated parameters.

In this way, the one or more processors may be used to identify particular environmental parameters that adversely affect a particular patient (e.g., elevate certain patient parameters and/or disturb sleep or rest) and/or that improve a condition of the particular patient (e.g., lower certain patient parameters and/or improve sleep or rest). For example, the one or more processors may identify that one patient is adversely affected by the voices of medical professionals, while another patient is soothed by the voices of medical professionals. Thus, the monitoring system may provide patient-specific or context-specific outputs that facilitate creation of a suitable environment for the particular patient. In some cases, the one or more processors may be used to generate a profile for the patient that indicates the patient's sensitivity to certain environmental parameters.

The disclosed monitoring systems and methods may be especially useful for sensitive, high-risk, and/or non-verbal patients, such as infants in a neonatal intensive care unit (NICU). Accordingly, the disclosed embodiments are presented in the context of the NICU to facilitate discussion; however, it should be appreciated that the disclosed embodiments may be adapted for use with various different types of patients in various different types of medical settings.

With the foregoing in mind, FIG. 1 is a block diagram of an embodiment of a patient monitoring system 10. As shown, the patient monitoring system 10 may include a control system 12 (e.g., electronic control system) that receives one or more patient parameters 14 and one or more environmental parameters 16. The control system 12 may receive the one or more patient parameters 14 and one or more environmental parameters 16 from one or more sensors, which may include one or more sensors positioned on the patient, one or more sensors positioned on a bed (e.g., a structure that supports the patient, such as a flat surface, table, and/or mattress), and/or one or more sensors otherwise positioned in a vicinity of the patient, for example. The one or more patient parameters 14 may include, but are not limited to, heart rate, other heart parameters, respiratory rate, oxygen saturation rate, brain activity, body temperature, sounds or vocalizations from the patient, and/or motion of the patient. The one or more environmental parameters 16 may include, but are not limited to, ambient temperature, ambient light, ambient sounds, and/or motion of the bed of the patient.

As discussed in more detail below, the control system 12 may include one or more processors that receive and process the one or more patient parameters 14 and the one or more environmental parameters 16 to identify a correlation (e.g., causal relationship) between the one or more patient parameters 14 and the one or more environmental parameters 16. In order to identify the correlation, the one or more processors may be used to monitor the one or more patient parameters 14 and the one or more environmental parameters 16 over time to detect an event, which may be a change (e.g., statistically significant change) in the one or more patient parameters 14 and/or one or more environmental parameters 16. Upon detection of the event, the one or more processors may analyze timing information (e.g., on an absolute and/or relative scale) for each of the one or more patient parameters 14 and the one or more environmental parameters 16. For example, upon detection of a change in the one or more environmental parameters 16, the one or more processors may be used to analyze the one or more patient parameters 14 during a time period (e.g., within 5, 10, 15, 20, 25, 30, or more seconds) after the change in the one or more environmental parameters 16. Upon detection of a change in the one or more patient parameters 14 during the time period, the one or more processors may determine that the change in the one or more environmental parameters 16 caused the change in the one or more patient parameters 14. For example, the one or more processors may determine that a loud ambient sound was followed by an increase in the heart rate of the patient. Thus, the one or more processors may identify that the loud ambient sound likely caused the increase in the heart rate of the patient.

Additionally or alternatively, upon detection of a change in the one or more patient parameters 14, the one or more processors may be used to analyze the one or more environmental parameters 16 during a time period (e.g., within 5, 10, 15, 20, 25, 30, or more seconds) before the change in the one or more patient parameters 14. Upon detection of a change in the one or more environmental parameters 16 during the time period, the one or more processors may determine that the change in the one or more environmental parameters 16 caused the change in the one or more patient parameters 14. For example, the one or more processors may determine that an increase in movement of the patient was preceded by a decrease in ambient temperature. Thus, the one or more processors may identify that the decrease in ambient temperature caused the increase in movement of the patient.

In some embodiments, the one or more processors may be used to identify the correlation based on a single event that indicates that the one or more patient parameters 14 were affected by the one or more environmental parameters 16. In some embodiments, the one or more processors may identify the correlation only after multiple events (e.g., 2, 3, 4, 5, or more) indicate that the one or more patient parameters 14 were affected by the one or more environmental parameters 16. In some embodiments, the one or more processors may determine and/or assign a confidence level to the correlation. The confidence level may be based on any of a variety of factors, such as a number of events that indicate that the one or more patient parameters 14 were affected by the one or more environmental parameters 16. For example, the one or more processors may determine that a loud ambient sound likely caused an increase in a heart rate of the patient based on a single event that indicates a correlation. However, the one or more processors may determine that a loud ambient sound likely caused an increase in a heart rate of the patient only after multiple events that indicate a correlation and/or the one or more processors may assign a confidence level to the correlation that increases with a number of events that indicate the correlation.

In some embodiments, the one or more processors may be used to characterize certain data (e.g., the sounds from the patient, the motion of the patient, the ambient light, the ambient sounds, and/or the motion of the bed of the patient) via various techniques, such as pattern recognition techniques. Thus, the one or more processors may be capable of identifying that one or more particular environmental parameters 16 affected (e.g., caused a change in) one or more particular patient parameters 14. For example, the one or more processors may be capable of identifying that a particular type of ambient sound (e.g., a beeping sound of a particular volume) caused a particular type of patient response (e.g., crying).

With respect to the sounds from the patient, the one or more processors may be used to characterize the sounds from the patient as having a particular volume, pitch, tone, and/or duration. The one or more processors may characterize the sounds from the patient as a particular type of sound (e.g., crying, screaming, laughing, talking, grunting) based on the volume, pitch, tone, and/or duration and/or using pattern recognition techniques, for example. The one or more processors may be used to characterize the motion of the patient as having a particular location, displacement, velocity, acceleration, and/or duration. The one or more processors may characterize the motion of the patient as a particular type of motion (e.g., rolling, moving arms, moving legs) based on the location, displacement, velocity, acceleration, and/or duration and/or using pattern recognition techniques, for example.

With respect to the ambient sounds, the one or more processors may be used to characterize the ambient sounds as having a particular volume, pitch, tone, and/or duration. The one or more processors may characterize the ambient sounds as a particular type of sound (e.g., beeping, clicking, alarms, talking, laughing, singing) based on the volume, pitch, tone, and/or duration and/or using pattern recognition techniques, for example. The one or more processors may characterize the ambient sounds as being from a particular device, such as an alarm from a pulse oximeter used to monitor the patient, an alarm on a nearby monitor, a sound associated with opening or closing a cover of the incubator, based on the volume, pitch, tone, and/or duration and/or using pattern recognition techniques, for example. The one or more processors may characterize the ambient sounds as being from a particular individual or type of individual, such as a parent of the patient, a primary physician of the patient, a primary nurse of the patient, a female, and/or a male, based on the volume, pitch, tone, and/or duration and/or using pattern recognition techniques, for example.

With respect to the motion of the bed of the patient, the one or more processors may be used to characterize the motion of the bed of the patient as having a particular contact or origination location, displacement, velocity, acceleration, and/or duration. The one or more processors may be used to characterize the motion of the bed of the patient as a particular type of motion (e.g., bump, rolling, shaking) based on the location, displacement, velocity, acceleration, and/or duration and/or using pattern recognition techniques, for example. With respect to the ambient light, the one or more processors may characterize the ambient light as having a particular brightness, color, and/or duration. The one or more processors may characterize the ambient light as being from a particular device, such as a blinking light from a nearby monitor, based on the brightness, color, and/or duration and/or using pattern recognition techniques, for example. The one or more processors may also receive inputs (e.g., from a medical professional) to assist with characterizing the one or more patient parameters 14 and/or the one or more environmental parameters 16. For example, the medical professional may provide voice samples to enable the one or more processors to later identify the voice of the medical professional and characterize ambient sounds as being from the medical professional.

The one or more processors may be used to build or generate a profile for the patient based on the data and the identified correlation(s). The profile may become more detailed over time as more data is received and analyzed. For example, the one or more processors may generate a profile that lists certain environmental parameters 16, such as ambient sounds and/or ambient light, that affect (e.g., adversely affect and/or positively affect) the patient. In some cases, the one or more processors may generate a more detailed profile that lists certain environmental parameters 16 with particular characteristics, such as talking above a certain volume and/or ambient light above a certain brightness, that affect (e.g., adversely affect and/or positively affect) the patient. In some cases, the one or more processors may generate a more detailed profile that lists both patient parameters 14 with particular characteristics and environmental parameters 16 with particular characteristics, such as that the heart rate, respiratory rate, movement of the patient decrease in response to talking below a certain volume (e.g., a positive effect) and/or that the patient moves and cries when exposed to ambient light above a certain brightness (e.g., a negative effect). In many cases, the patient's preferences and sensitivities may vary over time. For example, a premature infant's sensitivity to light may increase with age as their vision develops. Thus, the profile may update continuously or periodically over time as new data is collected.

The one or more processors of the control system 12 may also provide an output 18 (e.g., a visual output via a display screen and/or an audible output via a speaker). The output 18 may be indicative of the one or more patient parameters 14, the one or more environmental parameters 16, the correlation(s), the confidence level(s), and/or the profile, for example. In some embodiments, the output 18 may include a recommendation, such as a text message that suggests that speaking near the patient be limited to reduce negative effects on the patient or that suggests that the medical professional or other individual (e.g., patient's parent) speak to the patient to increase positive effects on the patient (e.g., prior to a procedure, when disturbed sleep is detected). In some cases, the one or more processors of the control system 12 may play a recording (e.g., the medical professional or other individual speaking, music) and/or cause other conditions (e.g., lighting) that has been determined to cause favorable patient parameters 14. In some embodiments, the output 18 may include one or more graphs that show the one or more patient parameters 14 over time, one or more graphs that show the one or more environmental parameters 16 over time, a numerical value of the one or more patient parameters 14 in real time or substantially real time, a numerical value of the one or more environmental parameters 16 in real time or substantially real time, a text message that lists prior or current patient parameters 14 and/or environmental parameters 16 (e.g., the patient is moving, the bed of the patient was bumped at a certain time). The output 18 may additionally or alternatively include a graph of the one or more patient parameters 14 and the one or more environmental parameters 16 over time with the data indicative of the correlation(s) highlighted. The output 18 may additionally or alternatively include a written list of the correlation(s) identified for the patient, and written list may include the confidence levels. The written list (alone or in combination with other information, such as recommendation(s)) may form the profile for the patient. In this way, the medical professionals treating the patient may be aware of and take care to avoid creating an environment with the environmental parameters 16 that adversely affect or otherwise disturb the patient and/or to create an environment with the environmental parameters 16 that positively affect the patient.

Figure 2:
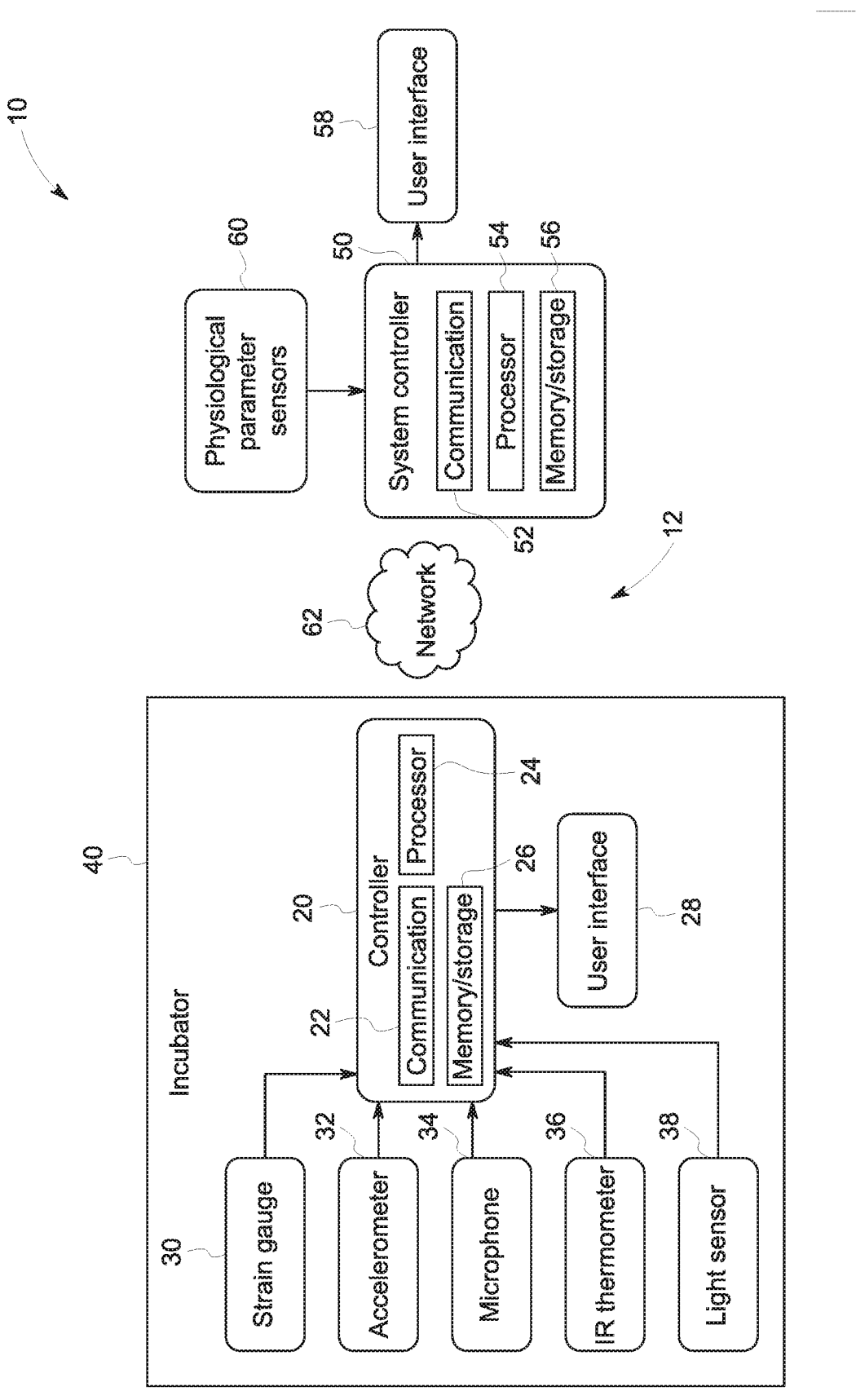
FIG. 2 is a block diagram of various sensing, processing, and output components that may be used in the patient monitoring system of FIG. 1, in accordance with an embodiment of the present disclosure.

FIG. 2 is a block diagram of various sensing, processing, and output components that may be used in the patient monitoring system 10, in accordance with an embodiment of the present disclosure. As shown, the patient monitoring system 10 includes a controller 20 (e.g., electronic controller, local controller, incubator-mounted controller) having one or more communication devices 22, one or more processors 24, and one or more memory/storage devices 26. As shown, the patient monitoring system 10 also includes one or more user interfaces 28 (e.g., local user interface, incubator-mounted user interface) and multiple sensors, such as one or more strain gauges 30, one or more accelerometers 32, one or more microphones 34, one or more infrared (IR) thermometers or cameras 36, and one or more light sensors 38. In the illustrated embodiment, the controller 20, the one or more user interfaces 28, the one or more strain gauges 30, the one or more accelerometers 32, the one or more microphones 34, the one or more infrared (IR) thermometers or cameras 36, and the one or more light sensors 38 are coupled to or otherwise supported by an incubator 40 (e.g., patient bed or other patient-supporting structure). It should be appreciated that the exemplary sensors described herein are not intended to be limiting, and the multiple sensors may include any of a variety of motion sensors (e.g., strain gauges 30, capacitive coupling devices, accelerometers, gyroscopes) and any of a variety of temperature sensors (e.g., IR thermometers or cameras, thermocouple), for example.

The one or more memory/storage devices 26 may include one or more tangible, non-transitory, computer-readable media that store instructions executable by the one or more processors 24 and/or data to be processed by the one or more processors 24. For example, the one or more memory/storage devices 26 may include random access memory (RAM), read only memory (ROM), rewritable non-volatile memory such as flash memory, hard drives, optical discs, and/or the like. Additionally, the one or more processors 24 may include one or more general purpose microprocessors, one or more application specific processors (ASICs), one or more field programmable gate arrays (FPGAs), or any combination thereof.

Advantageously, at least some of the sensors do not contact the patient (e.g., are physically separated from the patient), which may reduce interference with other equipment and/or may reduce irritation to the skin of the patient. More particularly, the one or more strain gauges 30 may be positioned on a substrate (e.g., a mattress, sheet, blanket, clothing, or other surface under or proximate to the patient) that enables the one or more strain gauges 30 to detect motion of the patient. The one or more accelerometers 32 may be positioned on the incubator 40 (e.g., on a frame of the incubator 40) to enable the one or more accelerometers 32 to detect motion of the incubator 40. The one or more microphones 34 may be positioned within a cover of the incubator 40 to enable the one or more microphones 34 to detect sounds of the patient and/or ambient sounds that reach an interior region within the cover of the incubator 40. The one or more IR thermometers or cameras 36 may be positioned within the cover of the incubator 40 to enable the one or more IR thermometers or cameras 36 to measure a body temperature of the patient and/or an ambient temperature within the interior region within the cover of the incubator 40. In some embodiments, the one or more IR thermometers or cameras 36 may also be capable of detecting ambient light that reaches the interior region within the cover of the incubator 40. The one or more light sensors 38 may include one or more light sensors 38 positioned within the cover of the incubator 40 to enable the light sensor 38 to detect ambient light that reaches the interior region within the cover of the incubator 40.

Figure 3:
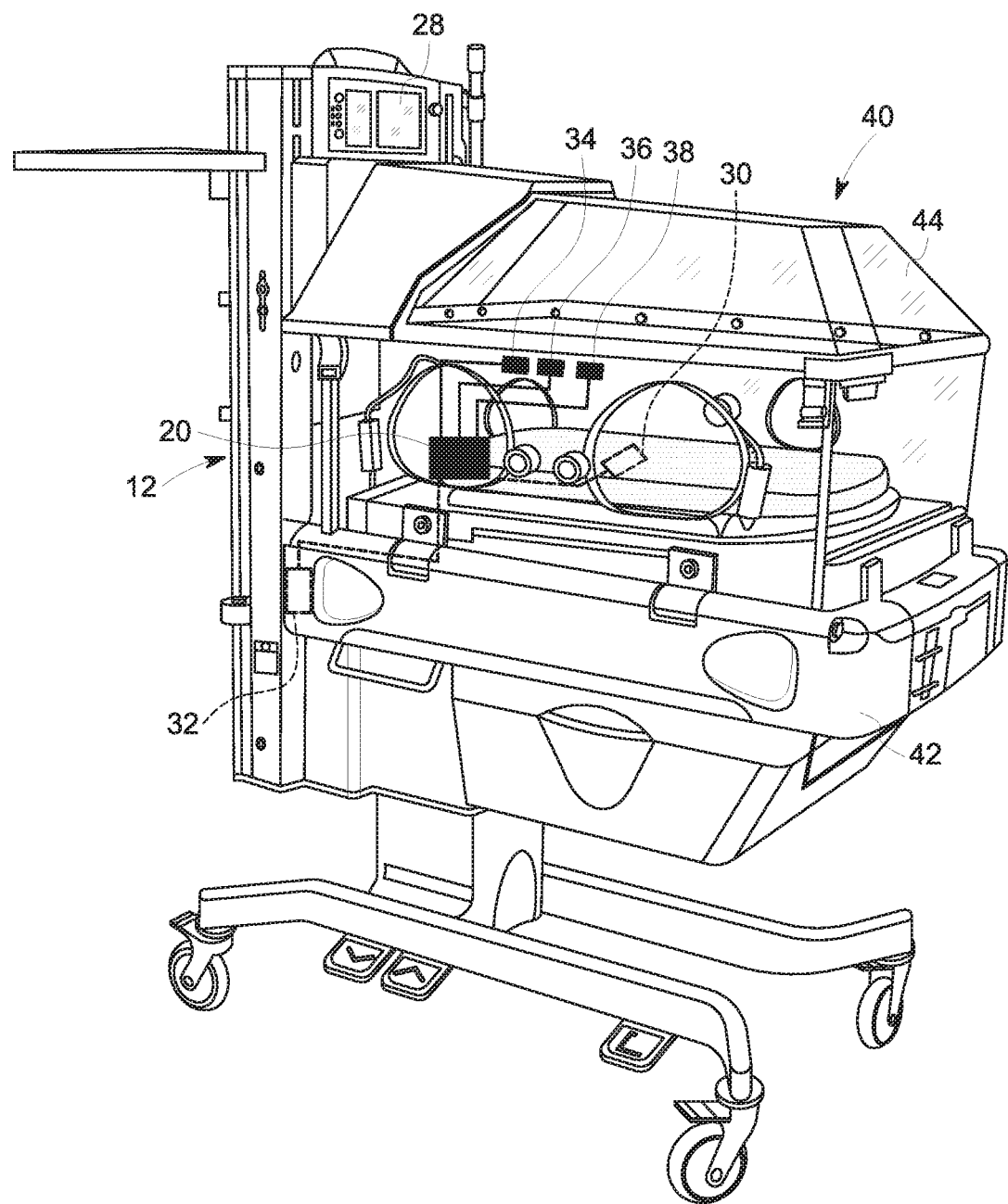
FIG. 3 is a perspective view of an incubator with at least some of the sensing, processing, and output components that may be used in the patient monitoring system of FIG. 1, in accordance with an embodiment of the present disclosure.
Figure 4:
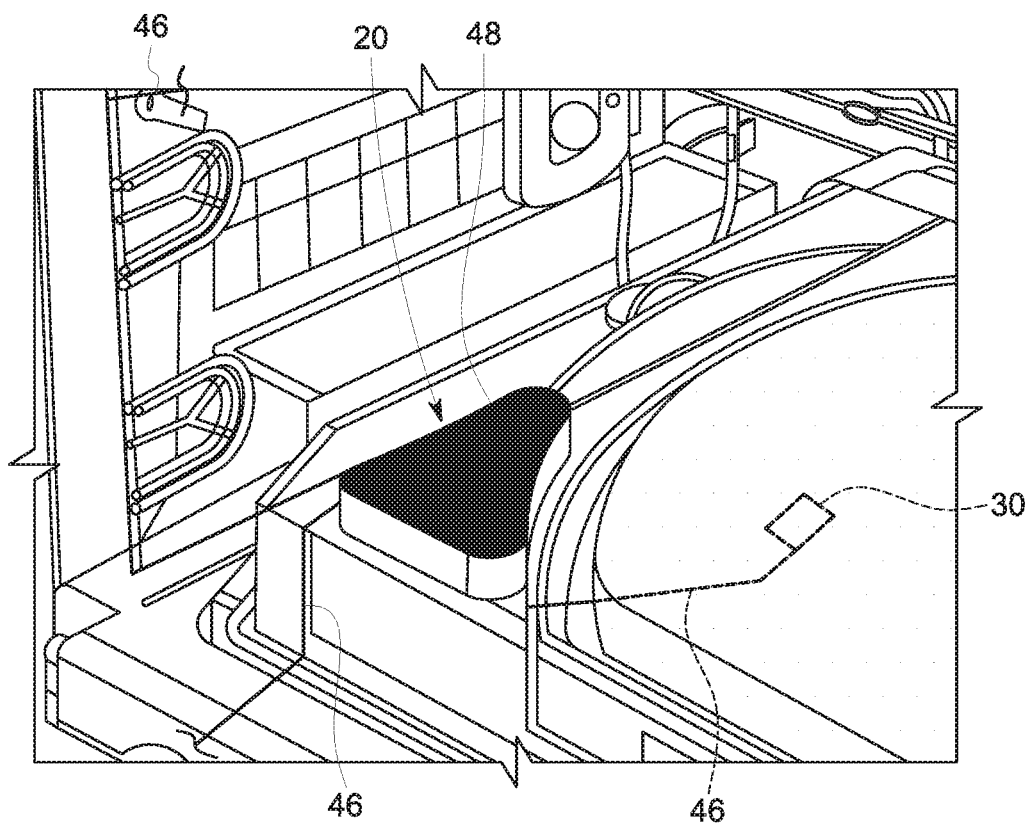
FIG. 4 is a perspective view of a portion of the incubator of FIG. 3, in accordance with an embodiment of the present disclosure.

For example, FIG. 3 illustrates an embodiment of the incubator 40 having a frame 42 and a cover 44, as well as the controller 20, the one or more user interfaces 28, the one or more strain gauges 30, the one or more accelerometers 32, the one or more microphones 34, the one or more IR thermometers or cameras 36, and the one or more light sensors 38. Similarly, FIG. 4 illustrates an embodiment of a portion of the incubator 40 with the controller 20 and wired connections (e.g., via respective wires 46) to some of the sensors that may be used in the patient monitoring system 10, such as the one or more strain gauges 30. As shown in FIG. 4, the components of the controller 20 may be housed within a housing 48, which may be supported on a portion of the frame 42 of the incubator 40 and positioned within the cover 44 of the incubator 40. In the illustrated embodiment, the housing 48 is supported within a recess (e.g., having a shape that corresponds to a shape of the housing 48) of the portion of the frame 42, although the housing 48 may be positioned in any of a variety of suitable locations. The wires 46 may extend to the various sensors and the one or more user interfaces 28. For example, at least one wire 46 may extend to at least one strain gauge 30 that is positioned under a sheet and/or under a mattress on which the patient rests.

In some embodiments, the cover 44 may be an opaque cover that blocks visualization of the patient and/or other components (e.g., at least some of the sensors of the patient monitoring system 10). The disclosed embodiments may enable the medical professional to monitor the one or more patient parameters disclosed herein without removing the cover 44 and/or without visualizing the patient. For example, the medical professional may monitor the motion of the patient without removing the cover 44 and/or without visualizing the patient. As noted above, it should also be appreciated that that various sensors may be used in other types of beds or support structures that may not have the cover 44. In such cases, the sensors may monitor the one or more environmental parameters in the vicinity of the patient and not within any cover 44.

Returning to FIG. 2, the patient monitoring system 10 also includes a system controller 50 having one or more communication devices 52, one or more processors 54, and one or more memory/storage devices 56. The patient monitoring system 10 further includes one or more user interfaces 58 (e.g., remote user interface) and one or more physiological parameter sensors 60. The one or more physiological parameters sensors 60 may monitor a heart rate, other heart parameters, a respiratory rate, an oxygen saturation of the patient, and/or brain activity, for example. In some cases, the one or more physiological parameter sensors 60 may include sensors and/or associated monitors capable of generating signals indicative of the various patient parameters disclosed herein, such as a heart rate monitor, a respiratory rate monitor, a pulse oximeter, an electroencephalogram monitor, an electrocardiogram monitor, a cerebral near-infrared spectroscopy (NIRS) monitor, or the like. The system controller 50 and the one or more user interfaces 58 may be remotely located (e.g., physically separated) from the incubator 40. The controller 20 and the system controller 50 may use their respective communication devices 22, 52 to communicate wirelessly via a network 62. The components of the system controller 50 may have any of the features disclosed above with respect to the controller 20.

The one or more physiological parameter sensors 60 may include sensing components that are in physical contact with the patient, such as electrodes that monitor electrical activity of the heart and that output signals that can be used to produce an electrocardiogram and determine a heart rate and/or other physiological parameters. However, some of all of the one or more physiological parameter sensors 60 may not include sensing components that are in physical contact with the patient. The one or more physiological parameter sensors 60 may provide data directly to the system controller 50 (e.g., via respective wired connections), which may be capable of processing the data to determine one or more physiological parameters. Alternatively, the one or more physiological parameter sensors 60 may provide data directly to one or more intermediate monitors (e.g., a heart rate monitor, a respiration monitor, and/or a pulse oximetry monitor via respective wired connections), which may process the data and/or send the processed data to the system controller 50 (e.g., via a wired connection or a wireless connection).

Thus, in operation, the system controller 50 may receive data measured by the one or more strain gauges 30, the one or more accelerometers 32, the one or more microphones 34, the one or more IR thermometers or cameras 36, the one or more light sensors 38, and/or the one or more physiological parameter sensors 60. The system controller 50 may process the data to identify a correlation (e.g., causal relationship) between the one or more patient parameters and the one or more environmental parameters in the manner discussed above with respect to FIG. 1. The system controller 50 may also provide the output, which may be indicative of the one or more patient parameters, the one or more environmental parameters, the correlation(s), the confidence level(s), and/or the profile, via the one or more user interfaces 58.

It should be appreciated that the various processing steps disclosed herein may be divided between components of the patient monitoring system 10 in any suitable manner. For example, the controller 20 may provide raw data (e.g., unfiltered data) to the system controller 50. Alternatively, the controller 20 may partially or fully process the data (e.g., filter, transform) and provide the processed data to the system controller 50. Furthermore, in some embodiments, the controller 20 may receive data measured by the one or more strain gauges 30, the one or more accelerometers 32, the one or more microphones 34, the one or more IR thermometers or cameras 36, the one or more light sensors 38, and/or the one or more physiological parameter sensors 60. Then, the controller 20 may process the data to identify a correlation between the one or more patient parameters and the one or more environmental parameters in the manner discussed above with respect to FIG. 1. The controller 20 may then output the processed data, the correlation, and/or other related information (e.g., the confidence level, the profile) to the system controller 50, to the one or more user interface 58, and/or to other remote devices (e.g., remote monitors, user interfaces, tablets) for further processing, storage, and/or display, for example. In some embodiments, the patient monitoring system 10 may not include the system controller 50 and/or the one or more user interfaces 58 located remotely from the incubator 40, but instead all of the processing and display steps may be carried out by the controller 20 and/or the one or more user interfaces 28 located at the incubator 40.

Figure 5:
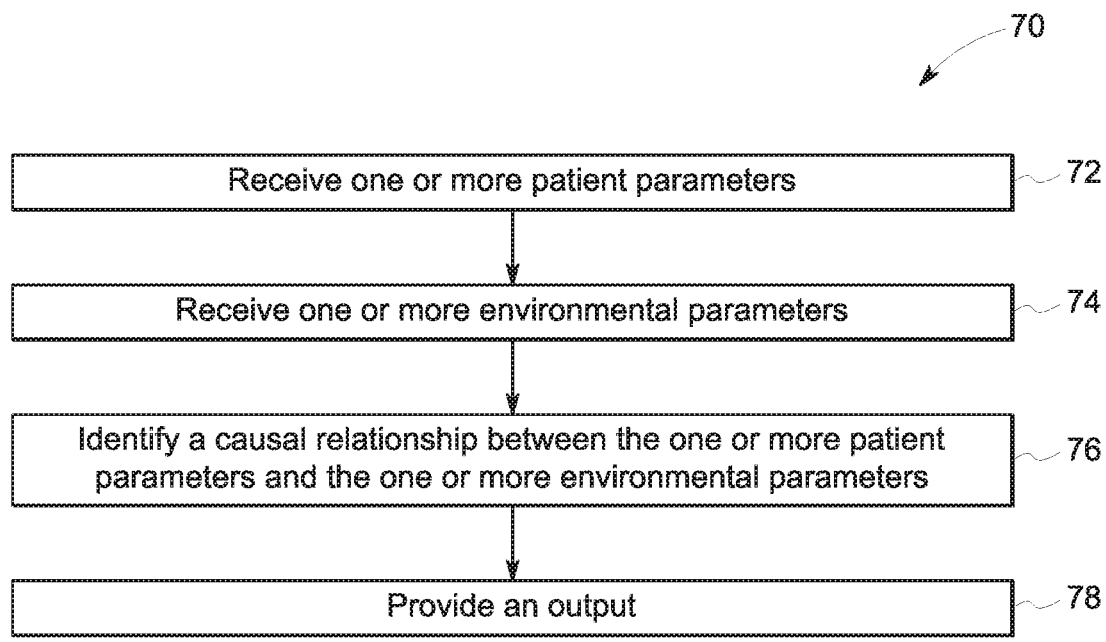
FIG. 5 is a flow diagram of a method of operating the patient monitoring system of FIG. 1, in accordance with an embodiment of the present disclosure.

FIG. 5 is a flow diagram of an embodiment of a method 70 of operating the patient monitoring system 10. The method 70 includes various steps represented by blocks. It should be noted that at least some steps of the method 70 may be performed as an automated procedure by a system, such as the patient monitoring system 10. Although the flow chart illustrates the steps in a certain sequence, it should be understood that the steps may be performed in any suitable order and certain steps may be carried out simultaneously, where appropriate. Additionally, steps may be added to or omitted from the method 70. Further, certain steps or portions of the method 70 may be performed by separate devices. For example, a first portion of a method 70 may be performed by the one or more processors 24 of the controller 20, while a second portion of the method 70 may be performed by the one or more processors 54 of the system controller 50. In addition, insofar as steps of the method 70 disclosed herein are applied to received signals, it should be understood that the received signals may be raw signals or processed signals.

In step 72, the one or more processors of the patient monitoring system may receive data indicative of one or more patient parameters. The one or more patient parameters may be measured by one or more sensors and may include, but are not limited to, heart rate, other heart parameters, respiratory rate, oxygen saturation rate, brain activity, body temperature, sounds from the patient, and/or motion of the patient.

In step 74, the one or more processors of the patient monitoring system may receive data indicative of one or more environmental parameters. The one or more environmental parameters may be measured by one or more sensors and may include, but are not limited to, ambient temperature, ambient light, ambient sounds, and/or motion of the bed of the patient.

In step 76, the one or more processors of the patient monitoring system may be used to identify a correlation (e.g., causal relationship) between the one or more patient parameters and the one or more environmental parameters. The correlation may be determined in any of a variety of ways. For example, the one or more processors may be used to detect an event, which may be a change (e.g., statistically significant change) in the one or more patient parameters and/or the one or more environmental parameters. Upon detection of a change in the one or more environmental parameters, the one or more processors may be used to analyze the one or more patient parameters during a time period after the change in the one or more environmental parameters to identify whether the change in the one or more environmental parameters was followed by a change in the one or more patient parameters. Similarly, upon detection of a change in the one or more patient parameters, the one or more processors may analyze the one or more environmental parameters during a time period preceding the change in the one or more patient parameters to identify whether the change in the one or more patient parameters was preceded by a change in the one or more environmental parameters. In this way, the one or more processors may be used to identify the correlation(s).

As discussed above with respect to FIG. 1, the one or more processors of the patient monitoring system may identify the correlation based on a single event that indicates that the one or more patient parameters were affected by the one or more environmental parameters. In some embodiments, the one or more processors may identify the correlation only after multiple events indicate that the one or more patient parameters were affected by the one or more environmental parameters. In some embodiments, the one or more processors may determine and/or assign a confidence level to the correlation. Furthermore, as discussed above with respect to FIG. 1, the one or more processors may characterize certain data to enable the one or more processors to identify more specific correlation(s) and/or the one or more processors may build a profile for the patient.

In step 78, the one or more processors of the patient monitoring system may provide an output. The output may be a visual output via a display screen and/or an audible output via a speaker. The output may include an indication of the one or more patient parameters, the one or more environmental parameters, the correlation(s), confidence level(s), and/or the profile. For example, the output may include a list of the environmental parameter(s) that adversely affect the patient. The output may include a recommendation. The method 70 may provide information to the medical professionals treating the patient to make the medical professional aware of any environmental parameters that adversely affect or otherwise disturb the patient and/or that positively affect the patient.

Technical effects include providing a patient monitoring system that uses multiple sensors to monitor one or more environmental parameters and one or more patient parameters. The disclosed patient monitoring systems improves patient monitoring techniques by correlating (e.g., determining a causal relationship) between the one or more environmental parameters and one or more patient parameters. In some cases, the disclosed patient monitoring systems improves patient monitoring techniques by generating a profile for the patient that indicates the patient's sensitivity to certain environmental parameter(s). The patient monitoring system may also include sensors that monitor the one or more environmental parameters and the one or more patient parameters without any contact with the patient. Accordingly, for at least these reasons, the patient monitoring system may be particularly useful for certain patient populations and/or in certain medical settings, such as for infants in a NICU.

This written description uses examples to disclose various embodiments, including the best mode, and also to enable any person skilled in the art to practice the embodiments, including making and using any devices or systems and performing any incorporated methods. The patentable scope of the application is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

The invention claimed is:

1. A system, comprising:
a memory or storage structure storing one or more processor-executable routines; and
one or more processors configured to execute the one or more processor-executable routines stored in the memory or storage structure, wherein the one or more processor-executable routines are configured and programmed to, when executed, cause the one or more processors to perform acts comprising:
receiving a first signal indicative of an environmental parameter of an environment;
receiving a second signal indicative of a patient parameter of a patient co-occurring or near in time to receiving the first signal;
analyzing changes in the first signal and the second signal to determine a causal relationship between the environmental parameter and the patient parameter;
determining a confidence level for the causal relationship; and
providing an output indicative of the causal relationship via a display screen, wherein the output comprises the confidence level;
wherein the one or more processors are configured to generate a patient specific profile for the patient based on the causal relationship, and the patient specific profile lists one or more environmental parameters that have affected the patient in the past; and
wherein the one or more processors are configured to update the patient specific profile as new data is collected.

2. The system of claim 1, wherein the environmental parameter comprises an ambient temperature, an ambient light, an ambient sound, or a motion of a bed of the patient.

3. The system of claim 1, wherein the patient parameter comprises a heart rate, a respiratory rate, an oxygen saturation rate, a body temperature, a sound from the patient, or a motion of the patient.

4. The system of claim 1, wherein the one or more processors are configured to determine the causal relationship by detecting a first change in the environmental parameter and detecting a second change in the patient parameter during a time period following the first change in the environmental parameter.

5. The system of claim 1, wherein the one or more processors are part of a system controller located remotely from the patient, and the one or more processors receive the first signal and the second signal via wireless communication.

6. The system of claim 1, wherein the one or more processors are configured to identify one or more characteristics of the environmental parameter and to identify one or more characteristics of the patient parameter.

7. The system of claim 6, wherein the output comprises an indication of the one or more characteristics of the environmental parameter and the one or more characteristics of the patient parameter.

8. An incubator system configured to house an infant, comprising:
a frame;
a cover configured to be coupled to the frame to cover a bed;
a plurality of sensors supported on the frame, positioned within the cover, or both, wherein the plurality of sensors are configured to monitor one or more environmental parameters of an environment around the infant and to monitor one or more patient parameters of the infant, and the plurality of sensors comprises one or more motion sensors configured to detect a motion of the bed of the infant and to detect a motion of the infant, one or more microphones configured to detect an ambient sound and a sound of the infant, and one or more temperature sensors configured to detect an ambient temperature and a body temperature of the infant; and one or more processors configured to receive one or more first signals indicative of the one or more environmental parameters of the environment from the plurality of sensors, to receive one or more second signals indicative of the one or more patient parameters of the infant from the plurality of sensors co-occurring or near in time to receiving the one or more first signals, analyze changes in the one or more first signals and the one or more second signals to determine a causal relationship between the one or more environmental parameters of the environment and the one or more patient parameters, to generate a patient specific profile for the patient based on the causal relationship, wherein the patient specific profile lists one or more environmental parameters that have affected the patient in the past, and to provide an output indicative of the causal relationship via a display, wherein the output comprises the patient specific profile; and wherein the one or more processors are configured to update the patient specific profile as new data is collected.

9. The incubator system of claim 8, wherein the plurality of sensors do not contact the infant.

10. The incubator system of claim 8, wherein the one or more motion sensors configured to detect the motion of the infant comprise one or more strain gauges.

11. The incubator system of claim 8, wherein the plurality of sensors comprise one or more physiological parameters sensors that are configured to monitor a heart rate of the infant, a respiratory rate of the infant, and an oxygen saturation of the infant.

12. A method, comprising:
receiving, at one or more processors, a first signal indicative of an environmental parameter of an environment;
receiving, at the one or more processors, a second signal indicative of a patient parameter of a patient co-occurring or near in time to receiving the first signal;
analyzing, using the one or more processors, changes in the first signal and the second signal to determine a causal relationship between the environmental parameter and the patient parameter;
generating a patient specific profile for the patient based on the causal relationship, using the one or more processors, wherein the patient specific profile lists one or more environmental parameters that affected the patient in the past; and
providing, using the one or more processors, an output indicative of the causal relationship via a display screen, wherein the output comprises the patient specific profile; and
updating the patient specific profile as new data is collected using the one or more processors.

13. The method of claim 12, wherein the environmental parameter comprises an ambient temperature, an ambient light, an ambient sound, or a motion of a bed of the patient, and wherein the patient parameter comprises a heart rate, a respiratory rate, an oxygen saturation rate, a body temperature, a sound from the patient, or a motion of the patient.

14. The method of claim 12, wherein analyzing the first signal and the second signal to determine the causal relationship comprises identifying at least one first change in the environmental parameter and identifying at least one second change in the patient parameter during a time period following the at least one first change in the environmental parameter.

15. The method of claim 12, comprising identifying the one or more characteristics of the environmental parameter, identifying one or more characteristics of the patient parameter, and providing the output indicative of the one or more characteristics of the environmental parameter and the one or more characteristics of the patient parameter, using the one or more processors.

* * * * *